(12) United States Patent
Sharf

(10) Patent No.: US 7,207,941 B2
(45) Date of Patent: *Apr. 24, 2007

(54) BIRTH MONITORING SYSTEM

(75) Inventor: Yehuda Sharf, Tel-Aviv (IL)

(73) Assignee: Barnev Ltd., Natania (IL)

( * ) Notice: Subject to any disclaimer, the term of this patent is extended or adjusted under 35 U.S.C. 154(b) by 429 days.

This patent is subject to a terminal disclaimer.

(21) Appl. No.: 10/479,826

(22) PCT Filed: Jun. 5, 2002

(86) PCT No.: PCT/IL02/00440

§ 371 (c)(1),
(2), (4) Date: Dec. 4, 2003

(87) PCT Pub. No.: WO02/098271

PCT Pub. Date: Dec. 12, 2002

(65) Prior Publication Data

US 2004/0236193 A1   Nov. 25, 2004

Related U.S. Application Data

(60) Provisional application No. 60/295,569, filed on Jun. 5, 2001, provisional application No. 60/295,573, filed on Jun. 5, 2001, provisional application No. 60/309,783, filed on Aug. 6, 2001, provisional application No. 60/338,671, filed on Dec. 11, 2001.

(51) Int. Cl.
*A61B 8/00* (2006.01)
*A61B 5/103* (2006.01)

(52) U.S. Cl. .................... 600/438; 600/588; 600/591

(58) Field of Classification Search ............... 600/407, 600/437, 438, 443, 449, 459, 300, 304, 587, 600/588, 591; 128/899

See application file for complete search history.

(56) References Cited

U.S. PATENT DOCUMENTS

| 2,924,220 A | 2/1960 | Lajos |
| 3,768,459 A | 10/1973 | Cannon |
| 4,141,345 A | 2/1979 | Allen et al. |
| 4,160,971 A | 7/1979 | Jones et al. |
| 4,488,558 A | 12/1984 | Simbruner et al. |
| 4,543,965 A | 10/1985 | Pack et al. |
| 4,677,967 A | 7/1987 | Zartman |
| 4,686,996 A | 8/1987 | Ulbrich |
| 4,867,177 A | 9/1989 | Urheim |
| 4,945,305 A * | 7/1990 | Blood .................. 342/207.17 |

(Continued)

FOREIGN PATENT DOCUMENTS

WO   WO 95/27963   10/1995

(Continued)

OTHER PUBLICATIONS

Lucidi, R. S. et al.; "Cervimetry: A Review of Methods for Measuring Cervical Dilatation During Labor"; Obstetrical and Gynecological Survey, vol. 56, No. 5; pp. 312-320.

(Continued)

*Primary Examiner*—Francis J. Jaworski

(57) ABSTRACT

A medical transponder, including an ultrasonic sensor that detects impinging ultrasonic waves and generates electrical signals in response thereto; an electrical connection which receives said signals; and an electromagnetic RF transmitter coupled to said electrical connection and which generates an RF signal in response to said detected waves.

46 Claims, 10 Drawing Sheets

U.S. PATENT DOCUMENTS

| | | | |
|---|---|---|---|
| 4,990,161 A | | 2/1991 | Kampner |
| 5,211,165 A | * | 5/1993 | Dumoulin et al. .......... 600/410 |
| 5,222,485 A | | 6/1993 | Jerath |
| 5,284,141 A | | 2/1994 | Eibling |
| 5,353,354 A | * | 10/1994 | Keller et al. ................ 382/128 |
| 5,388,579 A | | 2/1995 | Dowd et al. |
| 5,438,996 A | | 8/1995 | Kemper et al. |
| 5,515,853 A | | 5/1996 | Smith et al. |
| 5,538,005 A | | 7/1996 | Harrison et al. |
| 5,645,062 A | | 7/1997 | Anderson et al. |
| 5,671,736 A | | 9/1997 | Pettit et al. |
| 5,680,859 A | | 10/1997 | Urion et al. |
| 5,713,371 A | | 2/1998 | Sherman et al. |
| 5,727,547 A | | 3/1998 | Levinson et al. |
| 5,807,281 A | | 9/1998 | Welch |
| 5,817,035 A | | 10/1998 | Sullivan |
| 5,833,603 A | | 11/1998 | Kovacs et al. |
| 5,833,622 A | | 11/1998 | Meathrel et al. |
| 5,851,179 A | | 12/1998 | Ritson et al. |
| 5,851,188 A | | 12/1998 | Bullard et al. |
| 5,935,061 A | | 8/1999 | Acker et al. |
| 5,964,783 A | | 10/1999 | Grafton et al. |
| 6,039,701 A | | 3/2000 | Sliwa et al. |
| 6,169,914 B1 | | 1/2001 | Hovland et al. |
| 6,173,715 B1 | | 1/2001 | Sinanan et al. |
| 6,200,279 B1 | | 3/2001 | Paltieli |
| 6,242,004 B1 | | 6/2001 | Rault |
| 6,246,898 B1 | | 6/2001 | Vesely et al. |
| 6,261,247 B1 | * | 7/2001 | Ishikawa et al. ............ 600/587 |
| 6,270,458 B1 | | 8/2001 | Barnea |
| 6,332,089 B1 | | 12/2001 | Acker et al. |
| 6,352,513 B1 | | 3/2002 | Anderson et al. |
| 6,423,000 B1 | | 7/2002 | Berry |
| 6,454,716 B1 | * | 9/2002 | Zumeris ...................... 600/453 |
| 6,517,481 B2 | * | 2/2003 | Hoek et al. .................. 600/300 |
| 6,522,916 B1 | * | 2/2003 | Kwon ......................... 600/511 |
| 6,551,252 B2 | | 4/2003 | Sackner et al. |
| 6,636,769 B2 | * | 10/2003 | Govari et al. ................. 607/60 |
| 6,669,653 B2 | * | 12/2003 | Paltieli ....................... 600/588 |
| 2002/0028995 A1 | | 3/2002 | Mault |
| 2003/0114779 A1 | | 6/2003 | Paltieli |

FOREIGN PATENT DOCUMENTS

| | | |
|---|---|---|
| WO | WO 96/14586 | 5/1996 |
| WO | WO 98/09565 | 3/1998 |
| WO | WO 00/13039 | 3/2000 |
| WO | WO 00/21020 | 4/2000 |
| WO | WO 00/21203 | 4/2000 |
| WO | WO 00/46319 | 8/2000 |
| WO | WO 00/47644 | 8/2000 |
| WO | WO 00/51494 | 9/2000 |

OTHER PUBLICATIONS

Lueidi, R. S. et al.; "Cevimetry: A Review of Methods for Measuring Cervical Dilatation During Labor"; Obstetrical and Gynecological Survey, vol. 56, No. 5; pp. 312-320.

Wolfson, R. N. Ph.D. Thesis "An Instrument for the Continuous and Quantitative Determination of Fetal Descent by Measurement of Ultrasonic Transit Time (1975)"; pp. 1-233.

Ashley, S.; "Shape Shifters"; Scientific American, May 17, 2001; pp. 1-2.

* cited by examiner

BIRTH MONITORING SYSTEM

RELATED APPLICATIONS

This application is a U.S. National filing of PCT/IL/02/00440 filed Jun. 5, 2002. This application also claims the benefit under 119(e) of the following provisional applications: 60/295,569 filed 5 Jun. 2001, 60/295,573, filed 5 Jun. 2001, 60/309,783, filed 6 Aug. 2001 and 60/338,671, filed Dec. 11, 2001. This application is also related to PCT/IL/02/00441 filed Jun. 5, 2002, the disclosure of all of these applications is incorporated herein by reference.

FIELD OF THE INVENTION

The present invention relates to intrabody position monitoring systems.

BACKGROUND OF THE INVENTION

The birth of a human child is a complicated and traumatic process, of whose mechanical and geometrical aspects, surprisingly little is known. In a normal birth, the cervix dilates and a fetus is pushed out from a uterus and along a birth canal (e.g., the vagina), which lies between the pubic bones. This is described in greater detail, for example, in Williams Obstetrics Cunningham, Gary et al. Appleton & Lange 20th edition, the disclosure of which is incorporated herein by reference. Due to the relatively large size of the head of the fetus, not only is the head distorted by this passage, but it must also change direction and turn during the passage. First, however, the head must exit the uterus through the cervix, which requires the cervix to dilate a large amount.

It is common practice to monitor the progress of birth by measuring the degree of cervical dilation and monitoring contraction frequency (other parameters may be monitored as well, such as maternal heart rate). At a later stage, birth progress is estimated based on the location of the fetus's head. The locations along the birth canal are defined as stations. Currently, the gold standard of measurement for dilation, head orientation, station, effacement and cervical consistency is the human hand. However, this measurement method is not only unsanitary, it is also intrusive and inaccurate. Since the accuracy and meaning of the measurements depends on the person measuring (and even for a same person a 1 cm error is considered normal), when shifts change, measurements change. In addition, it is hypothesized that the cervix dilation increases momentarily during contraction, and fetus head location and orientation changes. These variations cannot be measured continuously in a reliable manner manually, reducing the amount of information available, for example, the effect of each contraction.

Various mechanical and electrical systems have been devised to measure cervical dilation and/or fetus head location, for example as described in "Cervimetry: A Review of Methods for Measuring Cervical Dilation During Labor", Obstetrics & Gynecology Survey, Vol. 55, No. 5, 2000 and U.S. Pat. Nos. 5,222,485, 6,039,701, 6,246,898, 5,935,061 and 6,200,279, the disclosures of which are incorporated herein by reference. These methods include, for example, Obstetric gloves incorporating a measuring string, finger mounted angular V calipers, Cervix mounted angular V calipers, induction transmitters and receivers clamped to two sides of the cervix opposite each other, a multi-switch membrane inserted in the uterus and pressed between the cervical internal os and the fetal head and magnetic filed position sensors.

A Ph.D. thesis By Robert Neal Wolfson, of September 1974, submitted to Case Western University, Department of Biomedical Engineering and titled "An Instrument for the Continuous and Quantitative Determination of Fetal Descent by Measurement of Ultrasonic Transit Time (1975)", the disclosure of which is incorporated herein by reference, suggests using ultrasonic waves and triangulation to determine a location of a fetus's head, using ultrasonic sensors placed inside the body to detect an ultrasonic field generated outside the body. One potential problem with this approach is that wires are required to connect to the ultrasonic sensors inside the body. Providing ultrasonic transmitters inside the body may not be a viable solution, due to their size. Using ultrasonic transmitter/receivers or reflectors may also be difficult, since they require transmission of ultrasound through tissue which may suffer from noise degradation and other effects (e.g., due to the many interfaces between different materials, significant accuracy and signal to noise problems may be experienced).

SUMMARY OF THE INVENTION

An aspect of some embodiments of the invention relates to a wireless transponder for intrabody medical uses, which detects an ultrasonic wave and generates an electromagnetic signal indicative of this detected wave, for example, an RF signal. In an exemplary embodiment of the invention, when the RF signal is detected, the relative or absolute time of arrival of the ultrasonic signs can be determined by measuring the relative time of arrival of the RF signal. In an exemplary embodiment of the invention, ultrasonic waves are utilized for ease of calculation of distances (e.g., relatively large differences in time of arrival), while the electromagnetic waves are used for ease of detection (e.g., noise level). Optionally, the electromagnetic-waves are used for determining additional information about the transponder, for example, its orientation and/or for transmission of identification information.

In an exemplary embodiment of the invention, the transponder includes a power source, for example, a battery or a power source that receives collects power from an imposed field, such as an RF field or a light field. Alternatively or additionally, the ultrasonic signal may power the transponder.

An aspect of some embodiments of the invention, relates to a method of distinguishing between a set of implanted transponders. In an exemplary embodiment of the invention, the transponders are designed to be activated and/or their signal detected by a single broadband antenna. However, each transponder uses a different frequency for reception and/or transmission. Optionally, the frequencies are defined as a series, for example, an arithmetic series. Alternatively or additionally, the frequencies are harmonics. Alternatively or additionally, each transducer transmits a set of frequencies, which encode ID information.

In an exemplary embodiment of the invention, the transponders are activated by an ultrasonic field and respond using narrow band RF fields, all of which are detected using a single RF antenna.

An aspect of some embodiments of the invention relates to a transponder for use in a body, in which a detector that detects a field is inserted in the body, for example, in a birth canal, and is attached to a wire at the end of which (e.g., outside the body) is a transmitter which transmits an indication of said detection. In an exemplary embodiment of the invention, the detection is a detection of an ultrasonic wave and the transmission is by electromagnetic wave. In a birth canal example, the transmitter is outside of the body, for example, attached to a hip.

An aspect of some embodiments of the invention relates to operating an ultrasonic transmission/RF reception system in a variety of complementary modes and/or using a plurality of receivers. In an exemplary embodiment of the invention, the modes include two or more of narrow-band transmission of ultrasound, narrow-band reception of RF, different geometries for different receivers, setting of trigger lines and regions of interest (ROI) by receiver aiming, broadband transmission, pulsed and/or burst transmission and continuous wave (CW) transmission. In an exemplary embodiment of the invention, narrow band reception provides better frequency discrimination in low signal to noise ratio (SNR) situations. Alternatively or additionally, antenna orientation is used to detect an orientation of a transducer, using phase differences between receivers. In some cases, orientation information is used even without positional information, for example, to determine fetal head orientation. Alternatively or additionally, an ROI setting is used to determine if a transmitter is within a desired (or out of a desired) location and for triggering more accurate detection of signals. In one example, a probe on a fetal head is detected when it leaves the uterus using a CW and ROI method and once detected, a narrow-band transmission method (e.g. using bursts) is used to obtain position information and phase information to obtain orientation information.

An aspect of some embodiments of the invention relates to a method of monitoring birth in which no known and fixed external reference position is used. Instead, the progress of the birth is determined by comparing the positions and/or orientation of cervical probes to that of one or more fetal probes. Optionally, a directional detector is used to identify if a probe exceeds its expected locations.

There is thus provided in accordance with an exemplary embodiment of the invention, a medical transponder, comprising:

an ultrasonic sensor that detects impinging ultrasonic waves and generates electrical signals in response thereto;

an electrical connection which receives said signals; and an electromagnetic RF transmitter coupled to said electrical connection and which generates an RF signal in response to said detected waves. Optionally, said electrical connection comprises circuitry. Optionally, said circuitry comprises a driving circuitry. Alternatively or additionally, said circuitry comprises a tuning circuitry.

In an exemplary embodiment of the invention, said transmitter has an output lower than said signal.

In an exemplary embodiment of the invention, said circuitry comprises a non-linear element which generates harmonics.

In an exemplary embodiment of the invention, said electrical connection drives said RF transmitter with substantially no delay relative to said ultrasonic detection.

In an exemplary embodiment of the invention, the transponder comprises a covering adapted to protect said transponder from fluids and pressures extant in a birth canal. Optionally, said covering is disposable.

In an exemplary embodiment of the invention, said transponder is small enough to avoid interfering with a birth process, when implanted in a birth canal.

In an exemplary embodiment of the invention, the transponder comprises an integral anchor adapted for attachment to cervical tissue.

Optionally, said transponder is powered solely by said detected ultrasonic waves. Alternatively, said transponder is powered by a transmitted power field.

In an exemplary embodiment of the invention, said transponder is powered by an integral power source.

In an exemplary embodiment of the invention, said circuitry modifies a frequency of said detected ultrasonic waves to generate a frequency for said transmitted RF waves. Optionally, said modification comprises a multiplication. Alternatively or additionally, said modification comprises a frequency shift. Alternatively or additionally, said circuitry comprises a variable element for generating different frequencies from a same base circuit. Alternatively or additionally, said circuitry resonates with said impinging waves to generate said transmitted waves. Alternatively or additionally, said circuitry comprises a modulation circuitry that uses said impinging waves to modulate said transmitted waves.

Alternatively or additionally, the transponder comprises at least one additional sensor and wherein said circuitry modulates said transmitted wave using a signal from said sensor.

In an exemplary embodiment of the invention, the transponder comprises a separate transmission antenna spatially displaced from said sensor by a wire, to a distance at least 10 times a maximal dimension of said sensor. Optionally, said wire is long enough to reach from a cervix to outside of a human body, through a birth canal. Optionally, said birth canal is a human birth canal. Alternatively or additionally, said birth canal is a an equine or bovine birth canal.

There is also provided in accordance with an exemplary embodiment of the invention, a method of detecting a transponder, comprising:

transmitting an ultrasonic wave to said transponder; and detecting an electromagnetic RF wave generated by said transponder in response to an interaction between said transponder and said ultrasonic wave. Optionally, the method comprises determining a time of flight of said ultrasonic wave from a difference between a time of arrival of said RF wave and a time of transmission of said ultrasonic wave. Optionally, the method comprises determining a location of said transponder by repeating said transmitting and said detecting from a plurality of transmitter locations. Optionally, said transmissions use at least two different frequencies for two different transmissions.

In an exemplary embodiment of the invention, the method comprises:

providing a plurality of transponders; and distinguishing between RF waves generated by different transponders. Optionally, distinguishing comprises distinguishing by frequency. Alternatively or additionally, the method comprises exciting said plurality of transponders using a broadband pulse.

In an exemplary embodiment of the invention, said detected RF wave has a frequency that is a small integer multiple of a frequency of said ultrasonic wave. Alternatively or additionally, said detection is near-field detection. Alternatively or additionally, detecting comprises detecting using a plurality of antennas; and determining phase information from said detecting. Optionally, the method comprises reconstructing an orientation of said transducer from said phase information.

In an exemplary embodiment of the invention, the method comprises inserting said transponder in a body. Optionally, the method comprises inserting said transponder in tissue adjacent a birth canal. Optionally, the method comprises monitoring a process of birth using said transmission and said detection. In an exemplary embodiment of the invention, said birth canal is a human birth canal. Alternatively, said birth canal is an equine or bovine birth canal.

There is also provided in accordance with an exemplary embodiment of the invention, a method of distinguishing between a plurality of intra-body transponders, comprising:

inserting a plurality of intra-body transponders into an animal body;

exciting at least one of said transponders using an excitation signal having a frequency;

detecting an electromagnetic RF signal including a contribution from at least one transponder, in response to said excitation signal; and identifying the transponder from a transponder frequency of said detected RF signal, wherein transponder frequencies of the transponders are a function of said excitation frequency. Optionally, detecting comprises broadband detection for a plurality of transponders simultaneously. Alternatively or additionally, said function is a multiplication function. Alternatively or additionally, said transponder frequencies are shifted by a fixed frequency from each other. Alternatively or additionally, exciting comprises exciting with a broadband signal that excites a plurality of transponders simultaneously. Alternatively or additionally, exciting comprises exciting with a narrow-band signal that selectively excites a transponder. Alternatively or additionally, exciting comprises exciting using an ultrasonic signal.

There is also provided in accordance with an exemplary embodiment of the invention, a transponder, comprising:

a detection sensor;

an anchor for attaching said sensor to a location of a body;

at least one wire electrically coupled to said sensor; and a transmitter, electrically coupled to said at least one wire and adapted to be placed at a distance from said sensor, which distance is at least 10 times greater than a maximum dimension of said sensor. Optionally, said detection sensor is an ultrasound sensor. Alternatively or additionally, said transmitter comprises an electromagnetic RF transmitter.

There is also provided in accordance with an exemplary embodiment of the invention, a method of collecting information from one or more medical transponders, comprising:

first transmitting an excitation signal to one or more medical transponders;

first receiving a first response of said transponder, said transmitting and receiving defining an interrogation;

second transmitting a second excitation signal to said transponder;

second receiving a second response of said transponder; and analyzing said responses to provide information about said transponder, wherein said first transmitting and receiving and second transmitting and receiving use different interrogation modes. Optionally, said interrogation modes are selected from continuous wave transmission, pulsed transmission, region of interest transmission, region of interest detection, phase detection, broad band detection and narrow band detection. Alternatively or additionally, said interrogations share at least one receiving antenna. Alternatively or additionally, said interrogations share at least one transmission antenna. Alternatively or additionally, said interrogations use the same transmission and reception antenna for both interrogation modes.

There is also provided in accordance with an exemplary embodiment of the invention, a method of monitoring a progress of a birth, comprising:

determining a position of at least one cervical transponder relative to a transmitter, which transmitter has a location not registered to fixed reference of the mother;

determining a position of at least one fetal transponder relative to said transmitter; and displaying a relative position of said at least one cervical transponder and said at least one fetal transponder. Optionally, the method comprises determining and displaying a relative orientation of said transponders.

There is also provided in accordance with an exemplary embodiment of the invention, a birth monitoring system, comprising:

an ultrasonic transmitter comprising at least one transmission element;

an electromagnetic RF receiver comprising at least one RF antenna;

at least two transponders adapted to attach to a cervix and which generate RF signals responsive to excitation by an ultrasonic signal;

a signal distinguisher which distinguishes between RF signals from different transponders; and a controller which analyzes said RF signals to produce an indication of a progress of a birth. Optionally, said indication comprises a dilation of said cervix. Alternatively or additionally, said indication comprises a station of a fetal head. Alternatively or additionally, said indication comprises an orientation of a fetal head. Alternatively or additionally, said system is adapted to be worn by a mother being monitored. Alternatively or additionally, said distinguisher is part of said controller.

BRIEF DESCRIPTION OF THE FIGURES

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which.

DETAILED DESCRIPTION OF EXEMPLARY EMBODIMENTS

Figure 1:
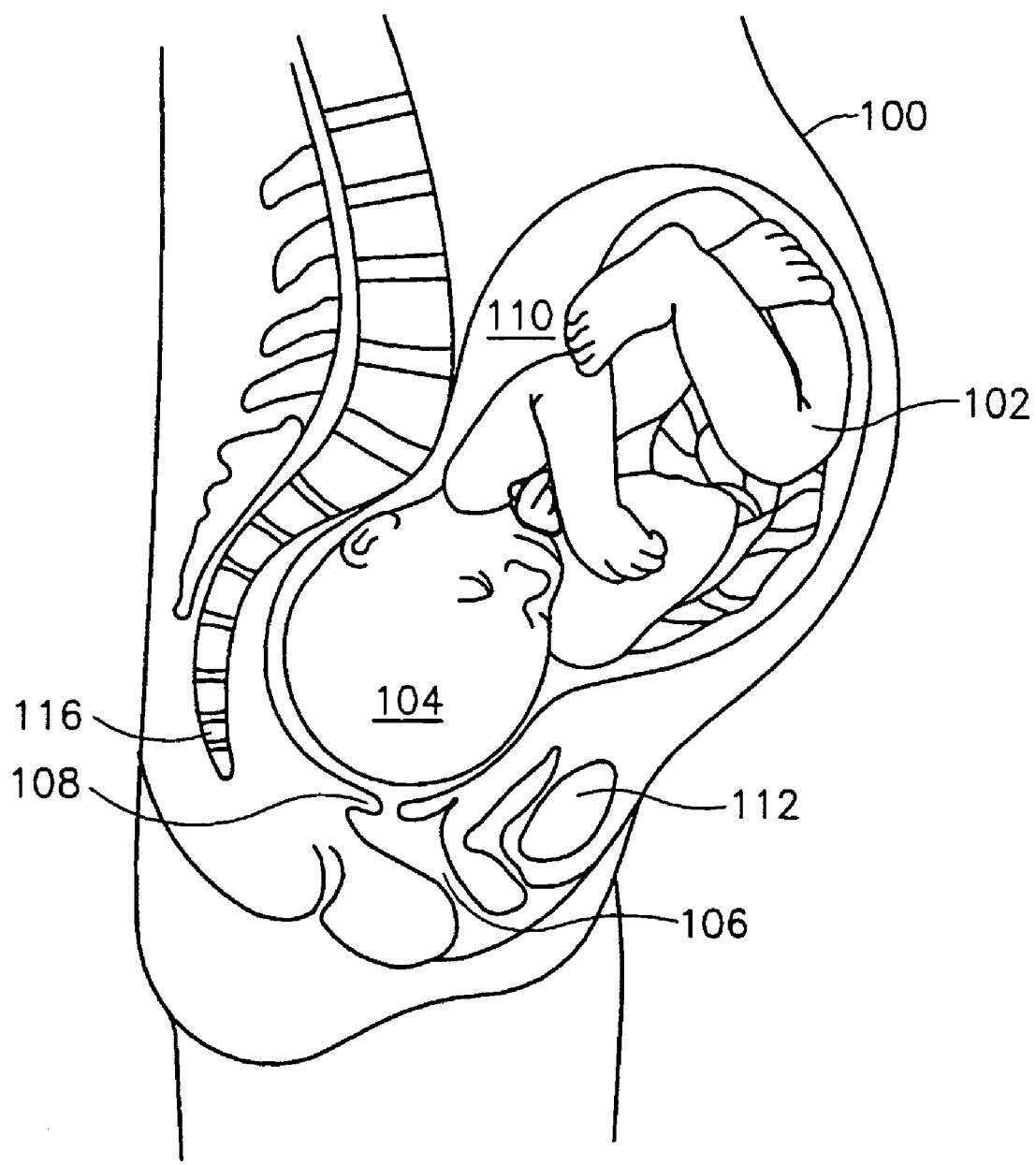
FIG. 1 is a side schematic view of a birth canal and uterus containing a fetus during delivery, on which the methods and/or apparatus of some embodiments of the present invention are applicable.

FIG. 1 shows is a side schematic view of a birth canal and uterus containing a fetus during normal vertex delivery, on which the methods and/or apparatus of some embodiments of the present invention are applied.

A supine mother 100 has a uterus 110 with a fetus 102 inside. In this figure, fetus 102 has its head 104 pointed forward, towards an opening 114 in a cervix 108. Once the cervix is dilated, fetus 102 will pass through a birth canal 106 and be born. Spine 116 and pelvic bone 112 constrain the path, forcing the fetus to bend and twist during the birthing (the side pelvic bone are not shown). This example is used for reason of convenience, however, various embodiments of the present invention may be usefully used also when the fetus has a different presentation than the one shown.

Figure 2:
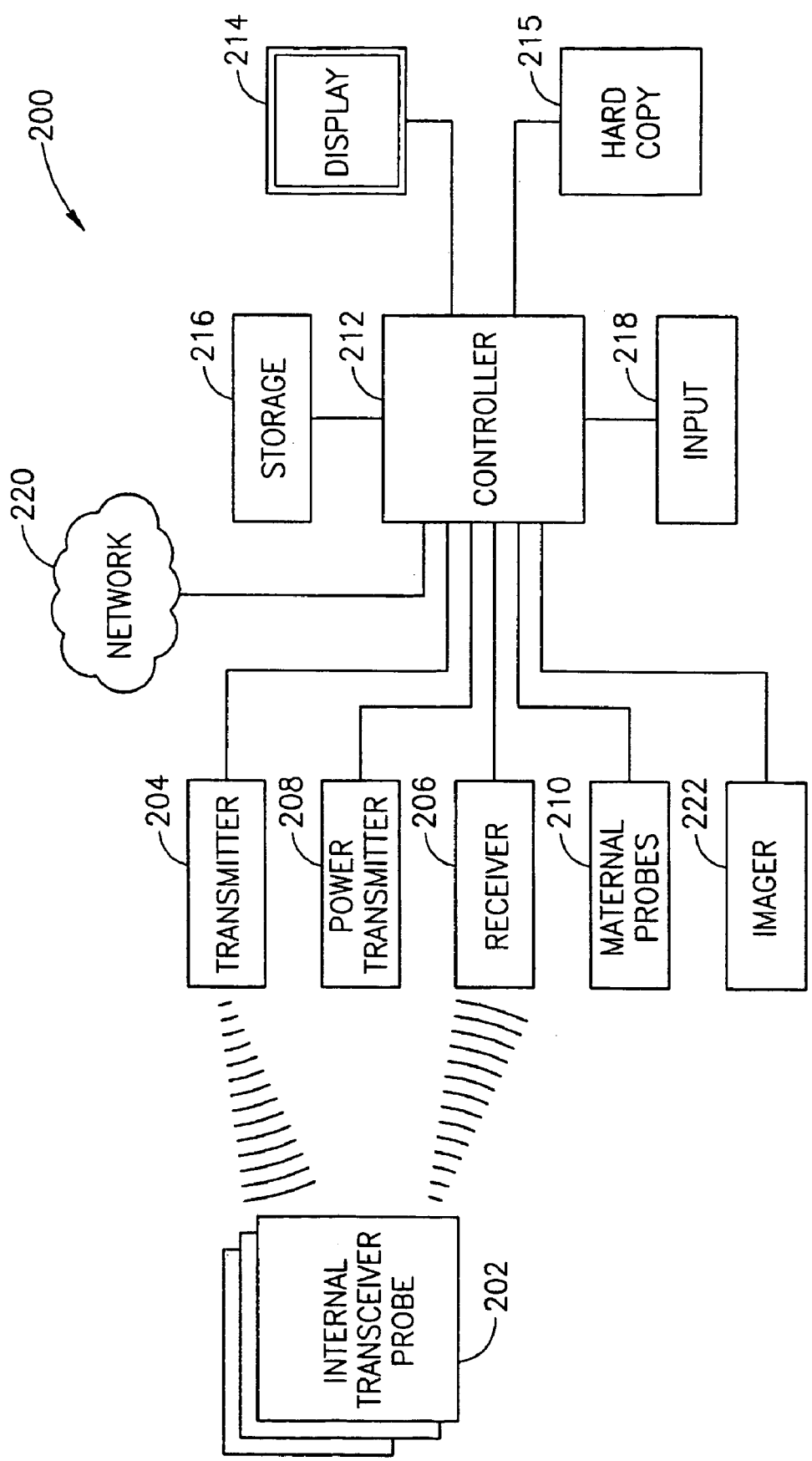
FIG. 2 is a schematic block diagram of a birth monitoring system in accordance with an exemplary embodiment of the invention.

FIG. 2 is a schematic block diagram of a birth monitoring system 200 in accordance with an exemplary embodiment of the invention. System 200 comprises at least one internal transducer probe 202, adapted to be attached to the cervix and/or the fetus.

In an exemplary embodiment of the invention, transducers 202 respond to an interrogation by an at least one transmitter 204, with a response that is detected by an at least one receiver 206. While in an exemplary embodiment of the invention, transmitter 204 is an ultrasonic transmitter and receiver 206 is an RF receiver, this is not essential in all embodiments of the invention, and in some embodiments the transmitter and receiver are combined as single unit (e.g., sharing an antenna).

Transmitter 204 and/or receiver 206 may operate using a continuous wave protocol or a pulsed protocol. Further, while in an exemplary embodiment of the invention, the signals are analog and possibly with little or no modulation, in an alternative exemplary embodiment of the invention, the signals are modulated and/or digital. Possibly, the transmission protocol is a networking protocol, such as bluetooth or IEEE 802 and its variants. Alternatively, there is no separate transmission protocol other than transponder probes 202 generating a response to signals that they detect.

Optionally, for example as described below, a separate power transmitter 208 is provided, to power and/or charge probes 202.

Optionally, for example as described below, additional maternal probes 210 or interfaces for such probes are provided, for example, contraction meters, oximeters and maternal and/or fetal ECG. Optionally, such probes are provided in addition or instead in internal transducer probes 202.

In an exemplary embodiment of the invention, a controller 212 is provided. This controller may have several functions, for example one or more of:

(a) calculate relative and/or absolute locations and/or orientations of probes 202;

(b) monitor such locations and/or orientations for generation of alerts, for example when a birth is or is not progressing as planned or expected or if a mishap happened or seems imminent;

(c) integrating and synchronizing probe locations to previous or current images and/or readings from other probes;

(d) extract signal information from the probe signals (described below);

(e) storing and retrieving relevant information from an optional storage 216, which may include, for example, a personal history, monitoring of previous births, an expected time table, previous measurements and/or their analysis from a current birth, a general baseline and/or calibration information;

(f) handling input from one or more input interfaces 218;

(g) generate displays for an optional display 214; and/or (h) generate output for an optional hard-copy device 215.

Optionally, a network connection 220 is provided, for example, to communicate with a central monitoring station (not shown), which may be useful for example in a hospital ward. In another example, the network connection is used to transmit a message, for example a text or graphic data message, to a remote location, for example to a spouse over a cellular telephone connection.

Figure 3A:
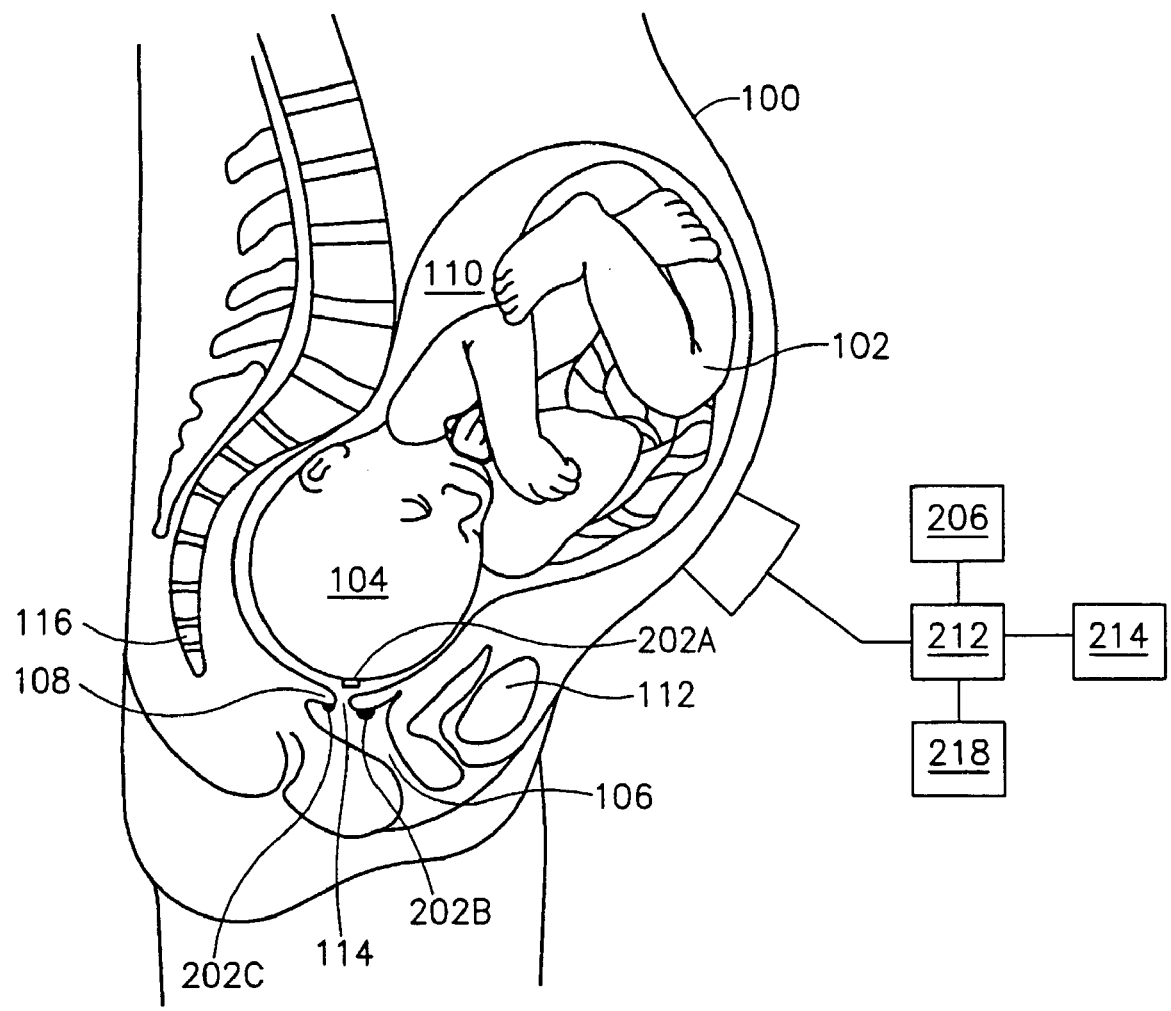
FIG. 3A is a showing of an application of the system of FIG. 2, to the physiology of FIG. 1, in accordance with an exemplary embodiment of the invention.

FIG. 3A shows an exemplary application of the system of FIG. 2, to the physiology of FIG. 1, in accordance with an exemplary embodiment of the invention. Not all elements of system 200 are shown, for clarity.

As shown two probes 202B and 202C are mounted on cervix os 108 and one probe 202A is mounted on head 104 (e.g., on the scalp). Other arrangements are possible, for example, more probes on the cervical os.

In an exemplary embodiment of the invention, transmitter 204 is an ultrasonic transmitter. Depending on the frequency used and the exact anatomy of mother 100, it may be desirable to locate transmitter 204 in a location where a clear ultrasonic path from transmitter 204 to probes 202 is available, for at least part of the birth process. Optionally, transmitter 204 is moved as needed. It should be noted that pelvic bone 112 is one element which may block, reflect or otherwise confuse ultrasonic signals. In an exemplary embodiment of the invention, transmitter 204 transmits using a beam with a shape, for example a cone or multiple cones, outside of which, probes 202 are not expected and/or expected not to respond. This may be used for selective excitation of probes and/or excitation based on location in the body. Optionally, the transmitter is inserted into the body, for example into the oral, vaginal or rectal cavities and/or into an artificially formed opening.

In an exemplary embodiment of the invention, after the probes are attached, a desired location for transmitter 204 is determined, in which the signal to noise level is high and multiple paths are not found or are not too disruptive (e.g., a calibration step). This may require repositioning of transmitter 204. Possibly, a plurality of possibly locations are determined during calibration and marked on the mother's skin, for example using a marker. Transmitter 204 may be attached to a fixed reference point on the mother's body (e.g., pubic bone 112), however, this is not necessary.

Receiver 206 may be located at any convenient location, with signal to noise being a consideration in some cases. Another possible consideration is lack of interference with a procedure. In a ward situation, multiple receivers may be located in a ward, to allow patients to ambulate. Optionally, controller 212 determines which transponders work as a set together using an identification signal of the transponders or based on similar reception properties of several signals, for example, temporal clustering or amplitude similarity. In general, controller 212 may reject some measurements and/ or apply smoothing, for example, erroneous signals or single unexpected valued signals.

In an exemplary embodiment of the invention, receiver 206 is integrated into or attached to a hospital bed, for example, its frame or under or in the mattress.

In an exemplary embodiment of the invention, receiver 206 has a localized field of view, which may be aimed (e.g., by moving or orienting receiver 206 and/or its antenna(s)), for example, at different parts of a patient. In one example, this localized field is used to detect when a probe has moved to a certain area (e.g., fetal head probe outside of a uterus).

While transmitter 204 and receiver 206 are shown with wired connections this is not necessary. For example, one or both may be wireless. In one example, transmitter 204 is a battery powered ultrasound source that generates a periodic signal. Such a periodic signal may be used to synchronize transmitter 204 and receiver 206. Alternatively or additionally, a wired or wireless connection is used to synchronize transmitter 204 and receiver 206. Synchronization may be used to provide (e.g., at receiver 206 or controller 212) an absolute time of flight measurement for the ultrasonic signals. Alternatively or additionally, only a relative time of flight is determined. Optionally, a reference transponder is used to provide a reference time of flight. While such a reference transponder may be located anywhere in the body, in one example, it is mounted on transmitter 204 (e.g., zero or low fixed time of flight).

In an exemplary embodiment of the invention, the delay time caused by the transponder circuit is ignored. Alternatively or additionally, it is corrected, e.g., at the controller, for example based on measurements of this delay. Alternatively or additionally, it is calibrated by checking the delay time of a transponder placed on the transmitter.

Various location determining methods are known in the art and may be used. For example, transmitter 204 can include three transmitters, each of which transmits an ultrasonic signal in turn to all probes. These signals may be the same and the probes need not differentiate between them, in some embodiments of the invention. Alternatively, they are differentiated, for example, by length, for example to assist in differentiation by controller 212. The time of flight at each probe is determined by controller 212 based on reception by receiver 206. Optimal positioning of transmitter 204 may also be accuracy related, for example it may include determining locations for which an error is minimal or below a threshold. The functions of transmitter 204 and receiver 206 may be reversed, for example using RF transmission and ultrasonic reception. Alternatively, fewer than three or more than three transmitters are used, for example, one, two, four or six transmitters.

In an exemplary embodiment of the invention, receiver 206 includes multiple (e.g., 1, 2, 3, 4, 5, 6 or more) axial RF antennas (e.g., coils), so that a phase and/or amplitude information can be detected and used to determine an orientation of probes 202 relative to receiver 206. Alternatively, each probe may include two or more spaced apart transponders. For RF probes, orientation information may be determined in ways known in the art. In some embodiments of the invention the position and/or orientation of receiver 206 is also dependent on the physiology and/or other consideration similar to those of transmitter 204. An exemplary calculation method for determining location in ultrasonic probes is described in U.S. Pat. No. 5,851,188, the disclosure of which is incorporated herein by reference.

In an exemplary embodiment of the invention, orientation information is used to determine the degree of cervical effacement and/or the degree and/or effect of contractions. Optionally, orientation information and/or location information is used to measure twisting of cervical os 108. Alternatively or additionally, orientation information is used to determine the passage of parts of fetus 102 past canal parts that have attached probes. Alternatively or additionally, orientation information is used to determine the orientation of head 104, for example to indicate twisting and turning of the head. Optionally, probes are attached to other parts of the fetus and assist in providing an indication of the layout of the fetus as a whole or at least those parts that are in the birth canal.

In an exemplary embodiment of the invention, the location and orientation data is collected for forming a baseline for the current patient or for other patients.

In an exemplary embodiment of the invention, when probe data is collected it is used in a comparative manner, for example, compared to an expected path. Such a path can be generated, for example, based on ultrasonic studies, insertion and tracking of a probe through the birth canal, previous case studies and/or a theoretical model. Optionally, the probe data is used to determine retrograde contractions and/or contraction strength (for example, by correlating non-positional maternal probe information, movement of fetal head during contraction and/or opening of cervix 108 during contraction).

It should be noted that there are several possible initial presentations of fetus 102. In an exemplary embodiment of the invention, the presentation is determined, for example by imaging and entered into input 218. Alternatively or additionally, other methods are used, for example, using manual checking.

In an exemplary embodiment of the invention, the process of using system 200 is as follows:
  (a) implantation of probes on cervix and/or fetus;
  (b) positioning of transmitter and/or receiver;
  (c) optional calibration of system and/or (re)positioning of transmitter and/or receiver;
  (d) collection of location and/or orientation data;
  (e) optional generation of alerts or other signal based on data processing;
  (f) optional attachment of additional probes, for example, to the fetal head when it appears;
  (g) tracking birth; and
  (h) removing probes during and/or after birth.

In an exemplary embodiment of the invention, system 200 shows various displays, for example, a 3D path, optionally overlaid on a 2D or 3D model or image of the birth canal, a dynamic Partogram, optionally showing not only changes but also indicating points where contractions had a significant or insignificant effect, such as retrograde contractions. Alternatively or additionally, a display shows short term behavior, for example cervical dilation, head station and orientation the last 10, 30, 60 or 120 seconds (e.g., to assess the effect of a single contraction). Alternatively or additionally, a display shows long term behavior, for example 30 minutes. Optionally, the effect of contractions is removed, for example by smoothing, averaging or other methods of artifact removal.

Optionally, various statistics, such as minimum, maximum average and variance are shown. Alternatively or additionally, additional time line information, for example that measured by various sensors (e.g., maternal, fetal heart rate, oximeter and/or EMG) is provided.

In an exemplary embodiment of the invention, the display is dependent on maternal position, for example showing different reference paths for the fetus for different positions. Alternatively or additionally, the various alerts are dependent on the maternal position. In an exemplary embodiment of the invention, the change in maternal position is detected by analyzing changes in the relative or absolute locations and/or orientations of the probe or using a reference probe (e.g., on the bed). Alternatively or additionally, phase information is used to detect a simultaneous change in orientation of several probes. Alternatively or additionally, an orientation or angular acceleration sensor is used to detect changes in maternal position.

Optionally, an imager 222 (FIG. 2) or an interface to an imager is provided, for example an ultrasonic imager. In an exemplary embodiment of the invention, a probe 202 or a different positioning probe is provided on the imager, so that the relative location of the image generated by the imager and the signals generated by the probes, can be reconstructed. Alternatively, fiduciary markers may be used and/or manual analysis may be performed.

Figure 3B:
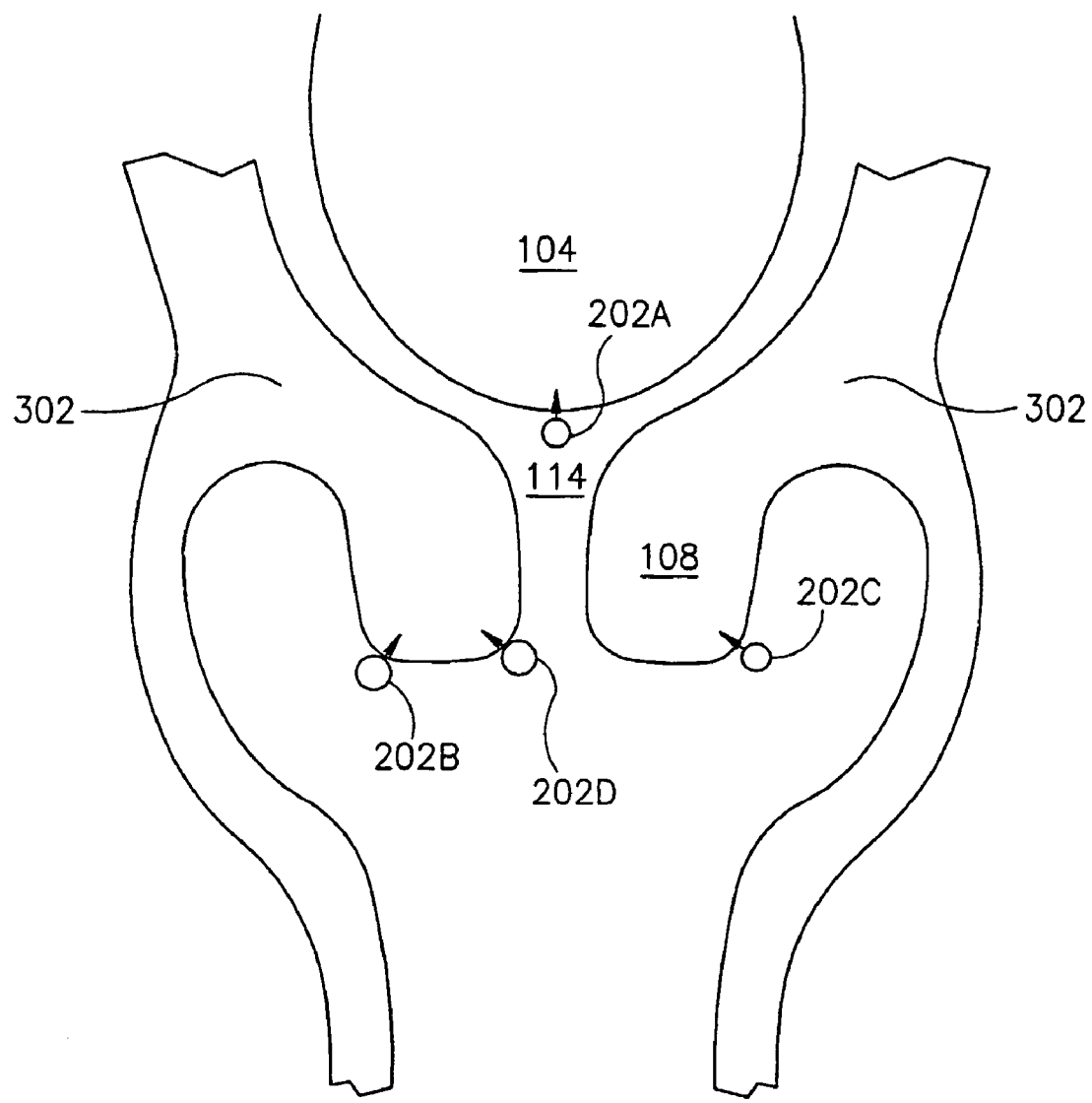
FIG. 3B is a detail view of the placement of transducer probes about a cervix, in accordance with an exemplary embodiment of the invention.

FIG. 3B is a detail view of the placement of transducer probes (shown in schematic form) about a cervix, in accordance with an exemplary embodiment of the invention.

In an exemplary embodiment of the invention, one (or more) probe 202A is placed on head 102, possibly, before it shows. Typically, patients report to the hospital after there is some cervical dilation, so the head is accessible. Alternatively, this probe may be placed at a later time, when the head is accessible. In some cases, the head probe and/or cervical probes may be implanted prior to labor beginning, for example at a pre-birth check up. This allows detecting the onset of birth, for example using an ambulatory system as described below.

In an exemplary embodiment of the invention, probes 202B and 202C are placed on opposite sides of cervix 108. Thus, as it dilates and cervical opening 114 widens, the probes are displaced from one another and the dilation may be measured as a correlation with this displacement. Optionally, during a calibration step, an initial distance between the probes may be ascertained, relative to an existing dilation of cervix 108. Optionally, a mapping table is provided, for example based on initial positioning of probe, that relates probe location and cervix dilation. This table may be generated, for example, by measuring manually and using system 200, on a group of test subjects.

Alternatively or additionally, two probes, for example probe 202B and a probe 202D may be placed on a same side of the cervix. These probes may be used to determine the effacement of cervix 108 and/or twisting thereof, when they move and reorient relative to each other. For example, when cervix 108 dilates completely (e.g., 10 cm), lines 302 may indicate the extent of cervix 108. Optionally, the relative orientation and/or location over time of probes (e.g., probes 202A, 202B, 202C and/or probe 202D) are used to determine if the probes were properly placed. It should be noted that if unusual results are generated it may be indicated to check the birth process manually or using a viewing tube scope, independent of whether the probes failed or there is a real physiological problem. In case of probe failure, the detached probes or new probes can be attached again and proper monitoring continued.

In an exemplary embodiment of the invention, one or more volumes of allowed and/or disallowed locations are defined for the probes. If a probe enters a disallowed volume or leaves an allowed volume an alert may be generated. Alternatively or additionally, these volumes are used to define stages in birth, for example, total effacement of cervix. The volumes may be dependent on maternal position. Alternatively or additionally, changes in location of probes outside volumes and/or other parameters are used to determine that a change in maternal position has occurred (e.g., lying down, side). In an exemplary embodiment of the invention, a head probe is allowed between the pelvic inlet and outlet. Alternatively or additionally, cervical probes are allowed between a plane of the pelvic inlet and a plane of ischial spines. Alternatively or additionally, changes of orientation are used for the same purposes, for example cervical probe orientation may indicate that a fetus is passing by or that the cervix is completely effaced.

While two probes are shown for the cervix in general, in an exemplary embodiment of the invention, more than two probes are used, for example, three or more probes around the circumference of the cervix. This may assist in preventing dilation estimation errors caused by uneven probe placement or uneven dilation of cervix.

In an exemplary embodiment of the invention, the effacement and/or dilation of cervix 108 are tracked, for example, to generate a distortion map of cervix 108. Generating such a map may also make it desirable to use additional probes, for example, four, five, six or more probes in all. While this map is useful in general for studying the cervix and determining the above mapping table, anomalies as compared to other studies may indicate a fault in the cervix which might cause premature birth or danger to mother or child. This fault can then be treated immediately or at least before a future pregnancy starts or reaches a danger point.

In an exemplary embodiment of the invention, the locations and orientations are made relative to a base location, for example, that of transmitter 204. However, this is not essential. Possibly, the cervical probes are used as a reference for themselves, since, at least in some parts of the birth process, they remain in a plane. In other parts of the birth process, it is the relative location of the head probe and the cervical probes that is important, not the absolute location.

In an exemplary embodiment of the invention, the head station is determined using a fixed reference, for example a probe on the outside of the body (or near front of birth canal) or using a known, fixed location of the transmitter. This position may be updated, for example if the probe is moved and/or calibrated, for example using an image or using manual checking. In an exemplary embodiment of the invention, the controller performs transformations so that the display (if any) matches a known standard, for example that of stations and/or expected changes in head orientation.

Figure 4:
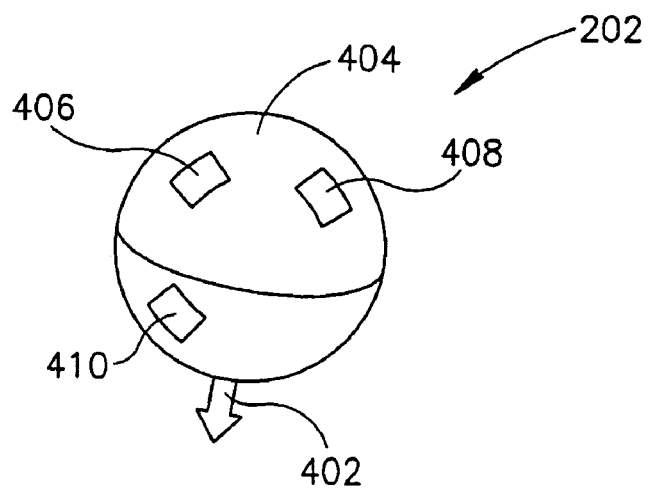
FIG. 4 is a schematic isometric showing of a single transponder probe in accordance with an exemplary embodiment of the invention.

FIG. 4 is a schematic isometric representation of a single transponder probe 202 in accordance with an exemplary embodiment of the invention.

Probe 202 comprises a body 404 and an attachment mechanism 402. Various attachment means may be used, for example those known in the art or such as described in the above referenced PCT filed on same date, the disclosure of which is incorporated herein by reference. In an exemplary embodiment of the invention, mechanism 402 comprises a bio-absorbable barbed spike, whose body dissolves after a time period, so that the rest of probe 202 detaches by itself.

In an exemplary embodiment of the invention, attachment mechanism 402 attaches probe body 404 rigidly enough that there is good ultrasonic coupling between the cervix and the probe. For example, the mechanism, (e.g., a curved wire) provides firm contact with no spaces. Optionally, a gel is used to ensure the lack of air bubbles and/or to provide suitable acoustic impedance (e.g., as a matching layer). In an exemplary embodiment of the invention, the attachment mechanism and/or the probe shape are designed to take into account the expected passage of a fetus against or adjacent the probe, with the associated friction, pressure and potential danger of damage to the fetus. For example, the attachment means is aligned along the path of fetal movement, the probe is streamlined and/or a control cable, if any, is made pliable.

Alternatively or additionally, the design takes into account an expected need for manual checking, for example being designed not to snag against a hand which is inserted and/or designed not to include a sharp barb which may snag a hand of a fetus.

While the shape shown is spherical, other shapes may be provided, for example, flattened on one side (e.g., to confirm to birth canal), cylindrical (e.g., to better fit some electronic packages) and/or oval (e.g., pill shaped). In some embodiments of the invention, a plurality of probes 202 are strung together, for example on an elastic thread (optionally designed to tear at low stresses, to prevent fetal strangulation), and these probes are attached around the external cervix os 108. The length of the tread may be, for example, 37 cm in circumference.

Body 404 may be formed of a bio-compatible material, such as a suitable plastic. Alternatively or additionally, body 404 is coated with a bio-compatible material. In some embodiments of the invention, the material selected is suitable for short (e.g., a few days) stay in contact with mucal members. Alternatively or additionally, body 404 is provided inside a disposable covering (e.g., a salable plastic bag), for example, to allow probe 202 itself to be reused and, possibly prevent damage by sterilization. Alternatively, body 404 and/or its coating is designed to permit sterilization. Alternatively, the probe is provided for one time use.

In an exemplary embodiment of the invention, the probe has a relatively small volume, for example, less than 2, 1, 0.5, 0.25 or 0.1 cubic centimeters, or any smaller or intermediate volume. This volume includes the volume of the attachment mechanism which protrudes into the birth canal.

While an ultrasonic sensor may be embedded wholly in body 404, in some embodiments of the invention, the sensor includes a surface portion, for example, as shown a patch 410. While a small patch is shown, a sensor may cover, for example, an entire hemisphere of body 404. Alternatively or additionally, patch 410 is for a different type of sensor, for example, a maternal ECG or EMG sensor or an oximeter. Alternatively or additionally, path 410 is used to measure properties of the cervix itself, for example thickness (e.g., a local ultrasonic transmitter/receiver), tension and consistency (e.g., hardness). Many different types of suitable sensors are known in the art for these measurements and may be used. Such sensors may be useful if probe 202 is attached to a part of fetus 102. The attachment mechanism 402 may also include a sensor, for example an attachment tension sensor, which may provide information about the attachment status of probe 202.

Alternatively or additionally, a sensor patch may be provided on an upper hemisphere of body 404, for example a patch 406 which may serve as a contact sensor for determining passage of fetus 102 against the probe. Alternatively or additionally, a power receiving contact or mechanism patch 408, may be provided, for example, an optical receiver or an electrical contact for contact recharging. Alternatively or additionally, patch 408 may be a signal antenna, for example, if IR communication is used instead of RF communication or if body 404 is impervious to RF radiation.

Optionally a control wire or safety tether (not shown) is attached to probe 202. This tether may be attached, for example to the hip and be used to prevent retrograde migration of the probe and/or to assist in removal thereof. In an exemplary embodiment of the invention, the attachment mechanism comprises a normally open release mechanism (e.g., a retraction spring) which is prevented from opening by a restraint (e.g., a pin). In an exemplary embodiment of the invention, pulling on the tether may activate the release mechanism (e.g., releasing the pin), so that no manual insertion is required for removing the probe. Alternatively or additionally, the attachment mechanism may weaken over time, so that when labor is over the probes may be removed with relatively little force.

In an exemplary embodiment of the invention, the control wire is attached to an antenna and/or circuitry that is outside the body, for example on the hip. Thus, the mother is not attached by these wires to a monitoring system, but the transmitted can be in a more convenient and/or better SNR location.

In an exemplary embodiment of the invention, body 404 is monolithic. Alternatively, it may be openable, for example for replacing a power supply.

Figure 5:
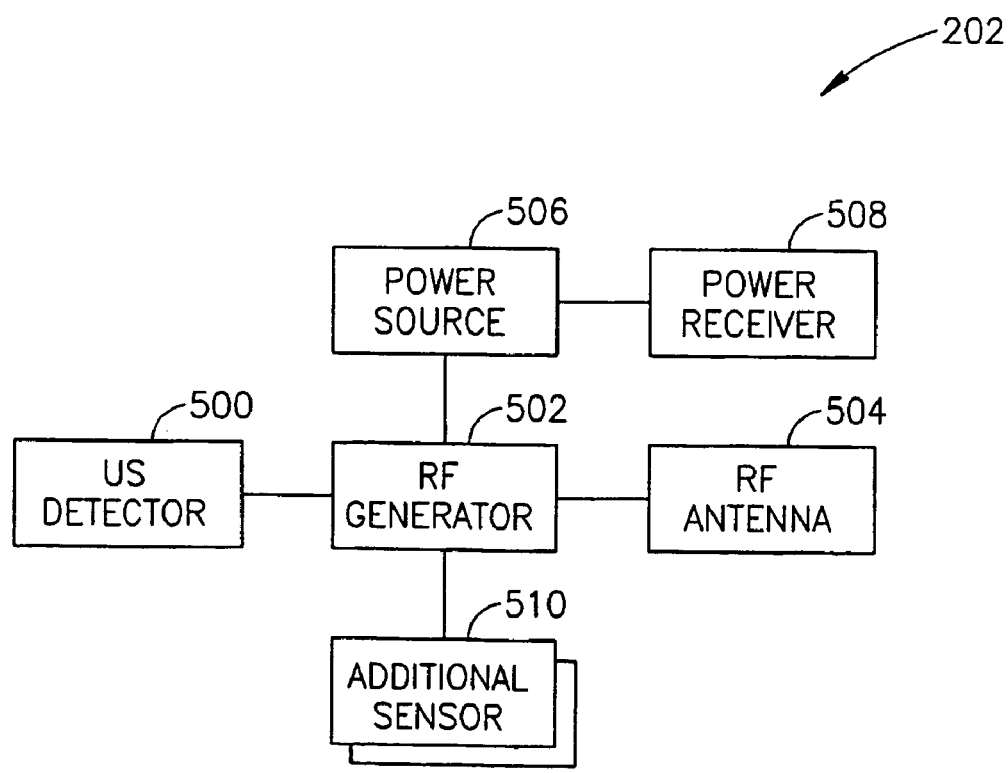
FIG. 5 is a schematic block diagram of a transponder probe in accordance with an exemplary embodiment of the invention.

FIG. 5 is a schematic block diagram of a transponder probe 202 in accordance with an exemplary embodiment of the invention. In an exemplary embodiment of the invention, an ultrasonic detector 500 receives an ultrasonic signal which is conveyed to an RF generator for generation and/or modulation of a signal. RF generator 502 may be powered by the ultrasound signals, alternatively, an optional power source 506 is provided. In some embodiments of the invention, a power receiver 508 is provided for charging or energizing power source 506, for example as described below.

The RF signal is passed to an RF antenna 504 for transmission, alternatively, other transmission methods may be used, for example, ultrasonic and IR.

Optionally, one or more additional sensors 510 are provided, whose input optionally modulates the output of RF generator 502.

While a single ultrasound detector 500 is shown, multiple detectors may be provided, for example, to assist in orientation determination of probe 202. The two detectors may share a single RF generator and antenna and/or other associated circuitry.

Optionally, probe 202 is designed (e.g., suitable power supply) to remain on head 104 even after birth, for example being used for wireless monitoring of the fetus's location, vital signs and/or for ID purposes.

Figure 6:
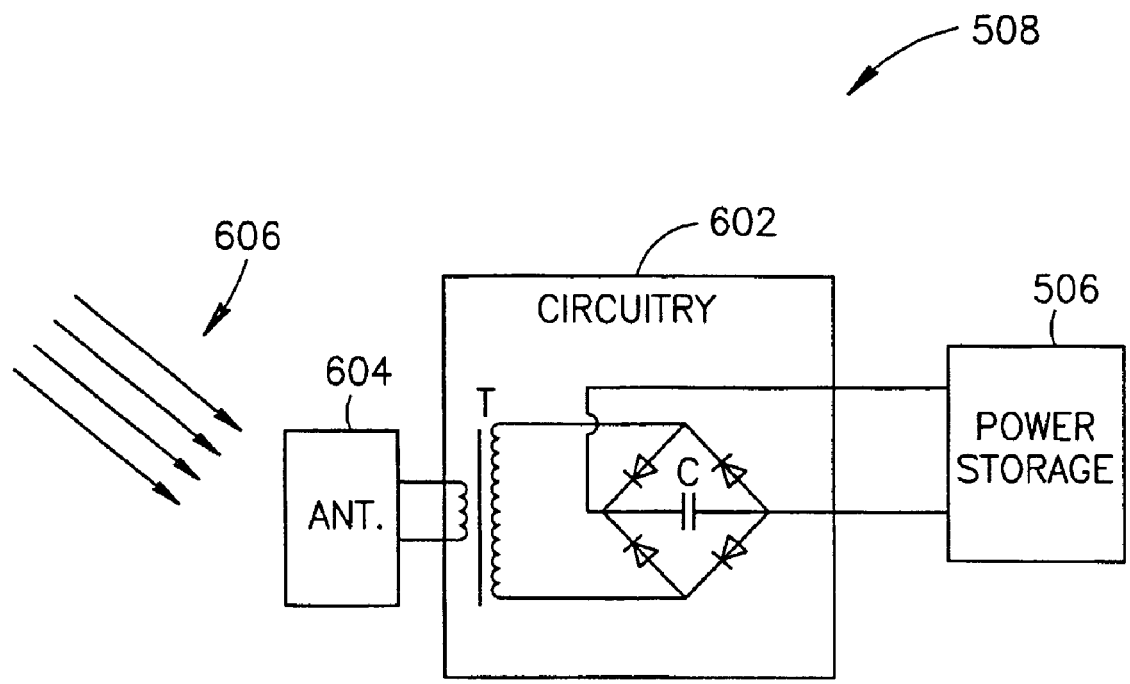
FIG. 6 is a schematic diagram of a mechanism for powering the transponder of FIG. 5, in accordance with exemplary embodiments of the invention.

FIG. 6 is a schematic diagram of a mechanism for powering the transponder of FIG. 5, in accordance with exemplary embodiments of the invention.

In an exemplary embodiment of the invention, a radiation field 606, for example, RF, light, ultrasound or low frequency magnetic field is received by an antenna 604 (or a photocell, or otherwise depending on type of field). Suitable circuitry (not shown) may be added, as needed and as known in the art, for example. The output signal is optionally rectified by a circuitry 602 and provided to charge a power source/storage 506, for example a capacitor. Optionally, circuitry 602 also increases the signal voltage, for example using a transformer or a DC—DC converter.

In an exemplary embodiment of the invention, radiation field 606 is intermittent, for example providing a charge when it can be provided (e.g., using a flash lamp). Alternatively or additionally, field 606 is provided before or during generation of an RF signal by probe 202, for momentarily powering of probe 202. In some cases, no power storage component is actually required. Alternatively, field 606 is continuous.

While separate power and signal detectors are shown, in some embodiments of the invention, two or more of the detector, the power receiver and the transmission antenna are shared. In one example, a piezoelectric crystal or other material is used both for transmitting RF and for receiving ultrasound. In another example, a same RF antenna is used for transmitting RF and for receiving RF power.

FIGS. 7A–7D are schematic circuit diagrams for transponding in accordance with an exemplary embodiment of the invention. In operation, when probe 202 detects a pulsed ultrasonic signal from transmitter 204 (or continuously, for a CW system), it generates an RF signal. In some embodiments, the received power of the ultrasonic signal is used to generate the RF signal. Alternatively, the received signal may be amplified, the output signal is amplified and/or the generation if the signal includes amplification. In one example, a scanning ultrasonic imaging beam can be used to set off a probe. As noted above, the imager may be coupled to system 200, optionally also including a position sensor to correlate positions and directions of gaze.

In some embodiments of the invention, the detected ultrasonic signal is used to directly generate an RF signal, for example of a same or similar magnitude. In others, it may be used to modulate a carrier wave or trigger the generation of an RF signal of an unrelated frequency.

As noted above, in some embodiments of the invention, it is desirable to distinguish between probes, while this may be done by limiting the reception bandwidth of each ultrasonic receiver, for example, by sensor design or using a filter, in other embodiments of the invention, distinguishing is provided by using a different carrier frequency, modulation and/or transmission frequency for each probe. In an exemplary embodiment of the invention, the probes are designed to generate a frequency F+nΔf, with different probes providing different values of n. In another embodiment, the frequency relationship is nF, where F is a base frequency. Frequency F maybe for example, fixed or it may depend on the ultrasonic excitation frequency.

It should be appreciated that multiple base frequencies may be used for various reasons, for example if multiple transmitters are used. The frequencies may be odd or prime multiples, so that that can be better distinguished at reception (e.g., if transponders double frequencies).

Figure 7A:
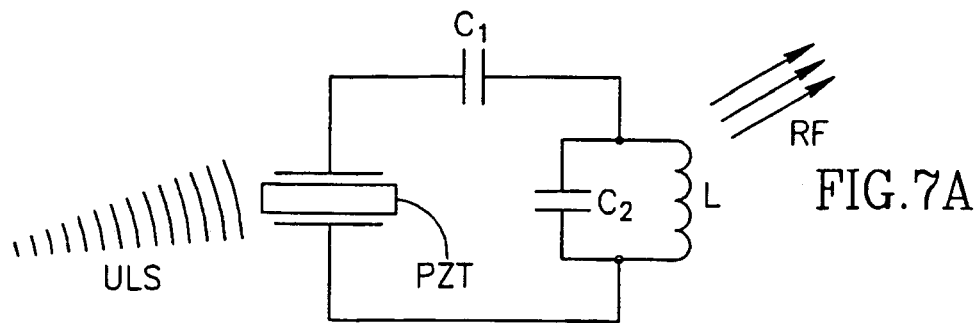
FIGS. 7A–7D are schematic circuit diagrams for transponding in accordance with an exemplary embodiment of the invention.

FIG. 7A shows a simplest circuit, where a coupling capacitor $C_1$ is connected to a resonance circuit composed of $C_2$ and L. This circuit is tuned to a preferred frequency F+nΔf, optionally taking into account the electrical properties of the rest of the probe (e.g., the capacitance of a piezo-electric detector). Optionally, n is set by varying the value of $C_1$. Optionally, $C_1$ may be varied by a screw, or modulated in real-time, for example, by sensor 510. Alternatively or additionally, the values of L or $C_2$ are varied.

Also shown in this circuit is a simple implementation of an ultrasound received, using a PZT crystal (or other suitable detector) as part of the circuit. In this example, the detected ultrasonic wave powers the RF transmission directly. As known in the art, the geometry of the detector may affect its sensitivity to various frequencies.

Figure 7B:
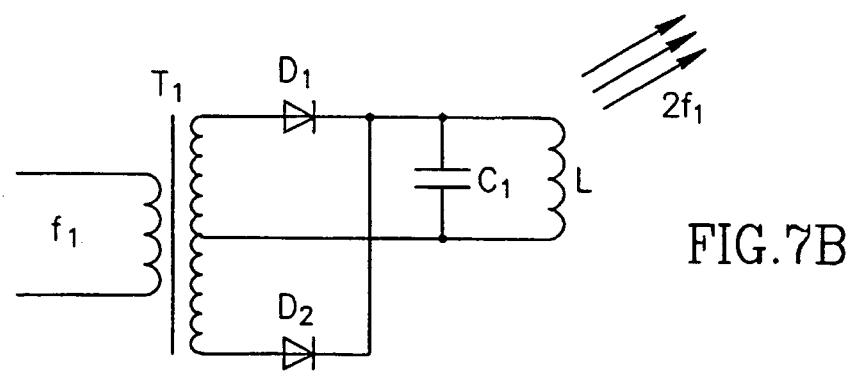

FIG. 7B shows a circuit where two diodes $D_1$ and $D_2$ are used to double a base frequency $f_1$ (e.g., detected ultrasound frequency or one generated by a crystal). $C_1$ and L form a resonance circuit that is tuned to the desired output frequency. $C_1$ may be tuned, for example as discussed in FIG. 7A.

Figure 7C:
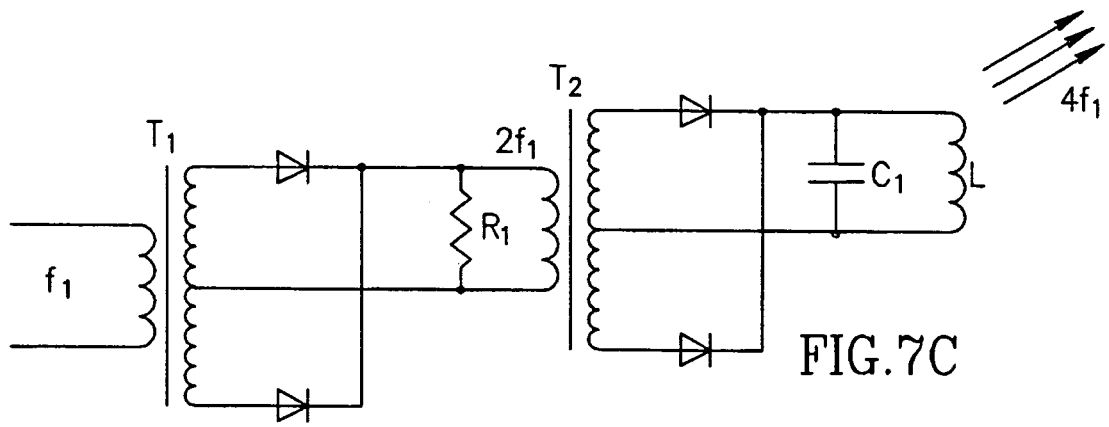

FIG. 7C shows a circuit where two circuits as in FIG. 7B are used to quadruple the frequency. Selective use of such circuits can be used to generate various multiples (e.g., for distinguishing purposes) for different probes.

Figure 7D:
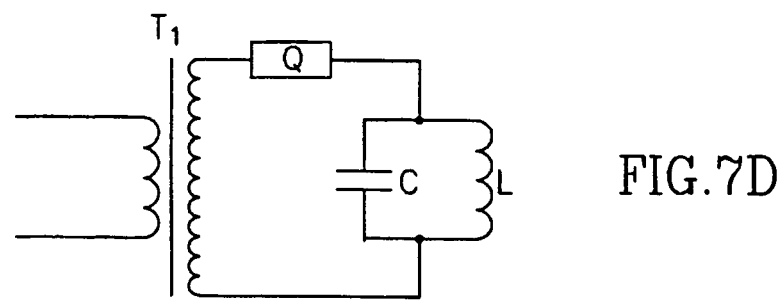

FIG. 7D shows a circuit using a nonlinear element Q, such as a tunnel or pin diode, to create harmonics of $f_1$. A resonance circuit formed by C and L are tuned to a desired output frequency.

Not shown is an option of generating a coded ID signal (e.g., 2, 4, 8 bits), for example using analog means or by providing a digital signal. Another option is providing digital circuitry for providing a networking protocol, such as bluetooth.

The transmission by the transponder may be, for example, directional or non-directional. In an exemplary embodiment of the invention, three orthogonal antennas are used to provide non-directional transmission. One potential benefit of directional transmission is using amplitude to estimate orientation and/or orientation change and/or for generating a trigger when orientation changes. Alternatively or additionally, directional transmission may have a better SNR. The antenna used may be, for example, a coil antenna or an integrated circuit antenna. Optionally, the antenna is provided in the body of the probe or printed on its outside.

Figure 8:
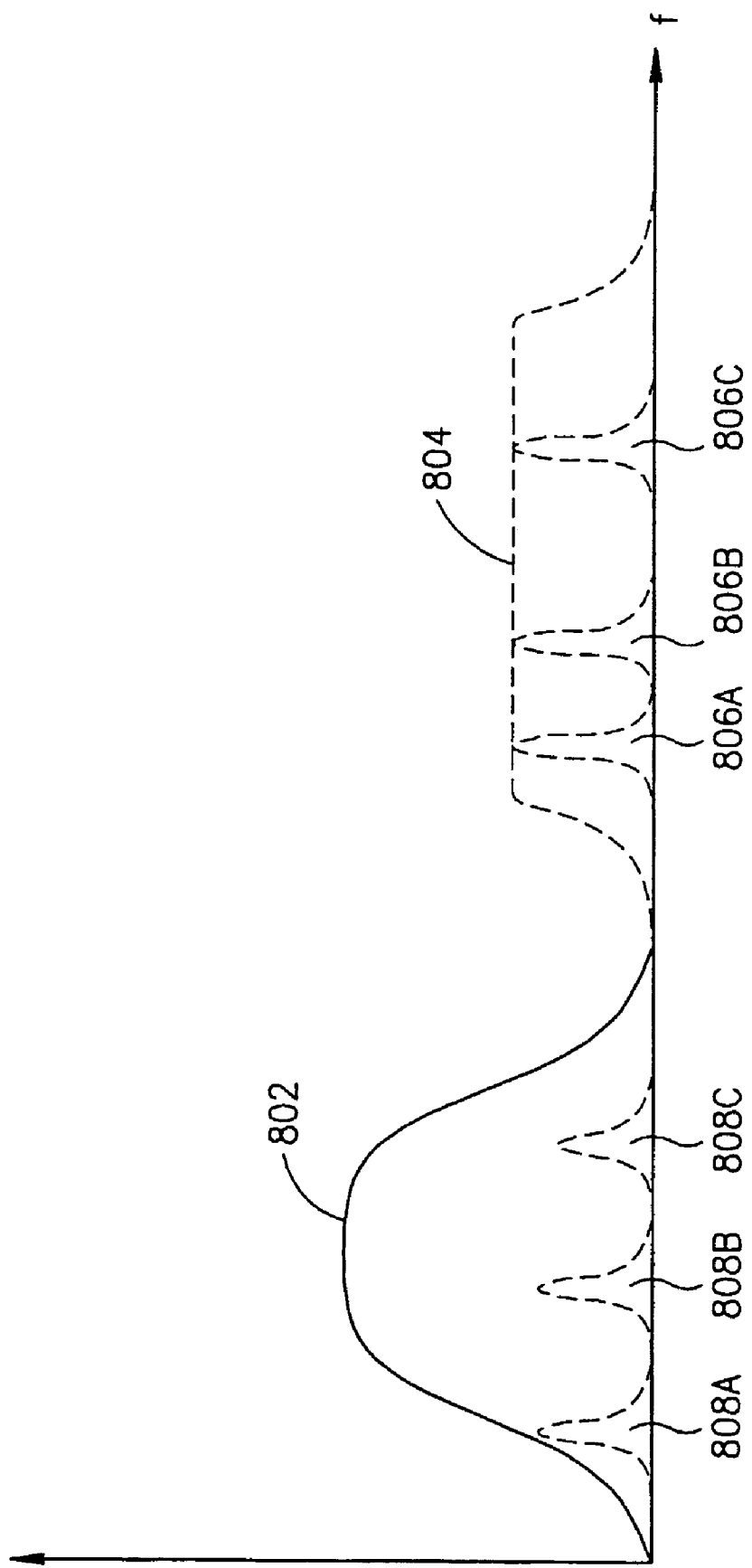
FIG. 8 illustrates relative bands of transmission and reception for a set of transducers in accordance with an exemplary embodiment of the invention.

FIG. 8 illustrates relative bands of transmission and reception for a set of transducers in accordance with an exemplary embodiment of the invention. Reference 802 indicates a transmission bandwidth of transmitter 204. As noted above, the actual transmission may be of several narrow bands within this range, for example, bands 808A–808C, possibly one for each transmitting element (e.g., there may be 1, 2, 3, 4 or more) in transmitter 204. Alternatively, bands 808 represent a limited detection or filtering ability of individual probes, for selective activation of probes. In an exemplary embodiment of the invention, a broad-band has a 1 Mhz center frequency with a width of 300 kHz. A narrow-band has a bandwidth of 20 kHz, for example. The exact base frequencies and widths may depend on the application and/or implementation (e.g., Q factor of transponder transmitter), as is well known in the art. The base frequency may depend, for example on the desired accuracy (for ultrasound) and/or type of noise sources. Other exemplary frequencies are between 100 kHz and 10 mHz or between 500 kHz and 3 mHz, with band widths of between 50 kHz and 500 kHz for broad band and between 1 kHz and 100 kHz for the narrow band.

Reference 804 shows an RF reception envelope of receiver 206. In some embodiments of the invention, however, the actual transmissions by different probes are narrow bands, for example 806A–806C, as shown. The exact frequency value may change in some embodiments, for example, depending on the instantaneous ultrasound transmission frequency, or if FM is used for providing sensor readings. Alternatively, AM modulation is used for providing sensor readings. The use of broadband ultrasound may be useful for allowing various frequencies to be generated by the probe and/or to provide more power and/or a better signal. In an exemplary embodiment of the invention, one of the probes transmits using a broad-band, which may be, for example, easier to detect and/or assist in distinguishing between the probes.

While shown separated, the two frequency bands 802 and 804 may overlap in part or completely. It should be noted that in many cases the ultrasonic wave will reach different transponders at different times. Thus, the transmitted RF waves will also be temporally separated, possibly with some overlap. Optionally, this temporal situation is used to assist in discrimination between transmissions. Optionally an extra ultrasound transmitter is provided so that at least three temporally delayed signal series are generated by the probes for all reasonable geometric configurations of the probes, e.g., with overlapping and/or non-delayed signals being ignored.

In an exemplary embodiment of the invention, the probes are provided in sets, with the bandwidth of the probes being designed to span the available range, for example to ensure distinguishing between the probes. Alternatively, other separation schemes may be used, for example, to allow additional probes to be provided at a later time.

In an exemplary embodiment of the invention, the probes are marked, for example to indicate their frequency and/or function (e.g., if each probe has a different sensor). Optionally, a probe includes an associated control cable, which may also be marked, which marking of the cable may allow for easier handling of dislodged probes.

Alternatively or additionally to bandwidth separation, different probes may transmit at different delays, thereby allowing distinguishing between probes. It is noted that this method may be more suitable when using a small number of probes (e.g. 3, 5, 10 or intermediate values). PCT applications PCT/US95/13232 and PCT publication WO 95/27963, the disclosure of which are incorporated herein by reference describe methods of distinguishing between RF transmissions based on various coding methods. These methods may be adapted to the present application, noting that if a small number of probes is used, separation may be easier. Alternatively or additionally, each probe may transmit at multiple frequencies, with the set of frequencies used identifying the probe. Alternatively or additionally, various signal characteristics, for example phase are used to identify the probes. For example, the current paths of a probe may depend on its orientation which may be expected to change at a rate lower than a threshold. For example, the speed of rotation of the fetal head is expected to be limited. If probe sampling is fast enough, this probe may be detected based on its orientation (e.g., based on phase signals) being close to a previous value. Optionally, a human decision may be used to assign location and/or signals to probes, at least for calibration purposes (e.g., based on a physician's indication which coded probed were attached where).

Alternatively or additionally, receiver 206 includes a directional and/or localized antenna. This may be used to detect signals from only a certain part of the body, possibly assisting in distinguishing between probes and/or generating a signal if a probe is outside (or inside) of an expected zone. Alternatively or additionally, such directional antenna are used to reduce noise levels. Alternatively or additionally, transmitter 204 is directional, so that not all probes are excited.

As noted above, the transmitters of the probes may be directional, alternatively or additionally to the receiver being directional. In addition, it should be noted that at the frequencies and distances described in some of the exemplary embodiments, the wavelengths dictate a near-field type of reception. Various combinations of directional and non-directional transmission and reception methods for the transducers and the receiver may be provided, some of which can use the same system, possibly requiring switching between antenna modes. Non-directional reception may require using more than one antenna.

In one exemplary mode, both transmission and detection are non-directional. This mode may not provide amplitude or directional information, but may ensure reception and/or good SNR in all orientations. In another example, the reception is directional and transmission is not. This mode may allow various region-of-interest triggering methods. Exemplary triggering methods are aiming a receiving antenna at a region of interest and detecting when a transponder enters that region. This may cause, for example, an alert to a human and/or changing of detection mode, for example to obtain position and/or orientation.

In another example, reception is non-directional and transmission is directional. This mode may allow orientation information to be generated (e.g., if the signals from the reception antennas are processed separately) and/or may improve SNR, since the transmitter can better focus its energy. Also, the transmitter may be simpler in some embodiments, as a simpler antenna may be used. In another example, both the transmission and the reception are directional. This mode may be useful for various types of triggering (e.g., based on probe orientation and/or on its position). This mode may also provide some information regarding the orientation of the transmitter.

It should be noted that there are two types of non-directional reception. In one, multiple antennas are linked together so that a signal can be received independent of the transmission orientation. In another, the signals from the different antennas can be processed, for example to provide the relative reception at each antenna, from which orientation information may be provided (e.g., if transmission is directional).

It should also be noted that there are two types of directional antenna. One type is directional with regard to the orientation relative to the transmission polarization. This may be implemented, for example, using a planar coil. Another type of directional antenna is a local coil detector, which detects signals mainly from a small locality (e.g., which may be placed near an area of interest). This may be implemented for example, using an antenna with a small effective surface area. In another example, a directional antenna that is sensitive to only some directions, is used.

In an exemplary embodiment of the invention, amplitude information is also collected, which may be used, for example, for estimating distances between the RF transponders and the receiver and/or estimating power of ultrasound transmission (e.g., disturbances and distance from ultrasound transmitter). Some orientation information may also be gleaned.

While it may add complexity to the transponder, in some embodiments of the invention, each transmission direction may use a different frequency and/or be at a different delay. This may assist in distinguishing the transponder orientation.

In an exemplary embodiment of the invention, receiver 206 and/or transmitter 204 are operated in various modes, with each mode providing information, and, optionally, the information provided from the various modes is combined, for example, to generate a more complete representation of the situation and/or assist in signal detection.

For example, if a CW mode may be used simply to elicit a response from a transponder. The signal, being longer, may be easier to detect, possibly using coherent detection methods. Then, a more informational method may be used. A pulsed mode may be useful for other detection methods. A narrow band method may be useful for selective excitation of probes (e.g., transmission in narrow band) and/or for better accuracy (in transmission or reception) and/or for better detection (e.g., using narrow band receivers). A chirp mode may be used for better accuracy in time of flight determinations. Phase determination (e.g., with one or more antennas) may be used for detecting orientation, possibly using CW. An ROI method may be used to reduce noise and/or to detect entry of a probe into a certain area (e.g., as a trigger for an alert or a trigger for changing detection mode).

Figure 9A:
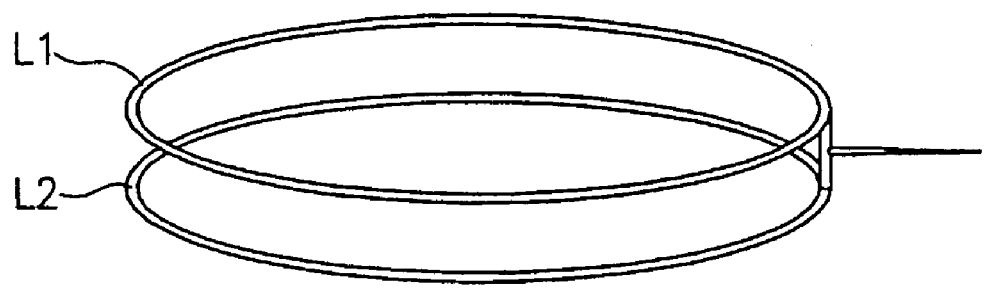
FIGS. 9A–9C show antenna and circuitry design for an RF receiver in accordance with an exemplary embodiment of the invention.
Figure 9B:
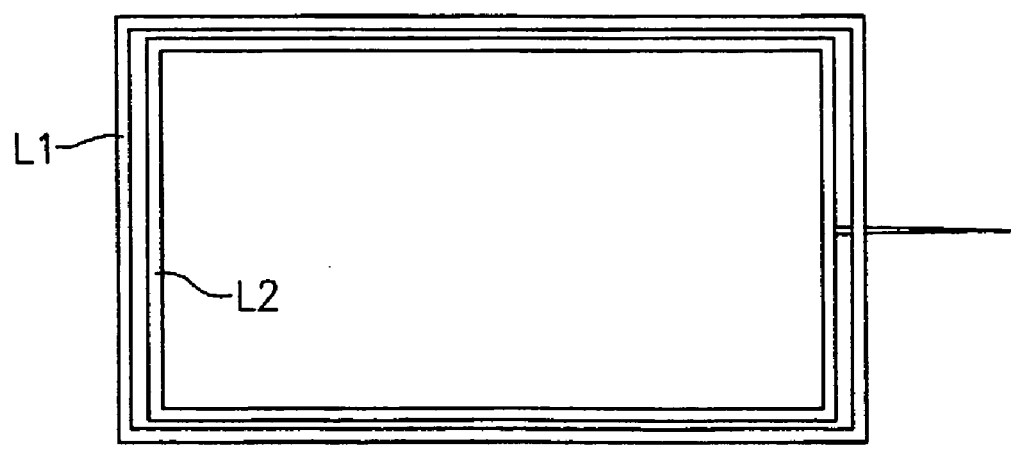
Figure 9C:
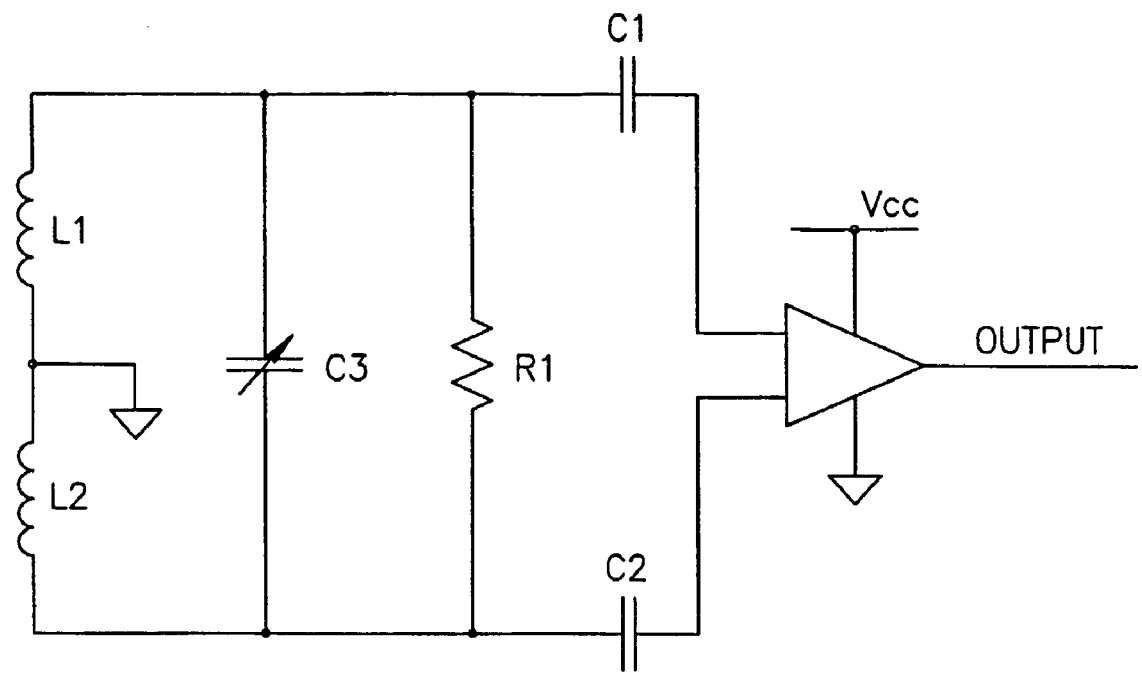

FIGS. 9A–9C show antenna and circuitry design for an RF receiver in accordance with an exemplary embodiment of the invention.

In the configuration of FIG. 9A, two spaced apart loops are shown, the radius may be, for example 40 cm. The distance between the loops can be, for example, 60 cm. In some cases, the patient is placed between the loops.

In FIG. 9B, the loops are substantially co-planar. This may be useful, for example, in placing an antenna under a pillow (e.g., embedded in a resin mat or between two sheets of fabric).

FIG. 9C shows an exemplary reception and pre-amplification circuit, which may be used, for example with the receiver antennas of FIGS. 9A and 9B. Other circuits, for example as known in the art may be used as well.

Referring back to FIG. 2, in an exemplary embodiment of the invention, system 200 is provided as a personal monitoring system, for example, as a device worn by a patient and possibly deployed by the patient or a caregiver. For example, controller 212 and optionally display 214 (e.g., visual and/or acoustic) are worn on a belt, which may include transmitter 204 and receiver 206. Controller 212 may include software for guiding a patient in a calibration or testing process. In an exemplary embodiment of the invention, display 214 shows graphically the progress of labor, for example using a 3D graphical model. Alternatively or additionally, system 200 is used in a hospital ward, with receivers provided where the patient is expected to ambulate. These receivers may be for detecting signals from probes 202 or from system 200, in which case, the use of a standardized wireless communication system in the whole hospital may be desirable. This set up, for example allows patients to ambulate, with an alert generated at a nurses station and/or by the device, when labor reaches a certain stage. The exact conditions for various alerts may be set, for example, at a nurse's station. A plurality of receivers may be installed in the ward, optionally, each such receiver generates a signal received by a receiver (possibly receiver 206) worn by the patient, so the patient can know she is in range.

In an exemplary embodiment of the invention, the device includes a link to a medical pump, for example, to automatically (or manually, for example via the nurse's station) control the provision of medication, for example, labor inducing or labor stopping medication. Alternatively or additionally, the device is integrated or linked with other wireless monitoring systems, for example, ECG and labor monitoring systems. The integration may comprise, for example, sharing of a wireless link or of a power supply.

In an exemplary embodiment of the invention, the probes are inserted by a patient. In one example, a shaped balloon or cap that fits over the cervix is provided. Weakly attached to this balloon or cap are adhesive probes. The patient inserts the cap and waits for the adhesive to attach. For example, the adhesive may be coated with a layer that dissolves after a minute, to allow time for insertion. A personal cervix applicator, designed for bringing an applicator to the lips of the cervix and which may be used for probes (e.g., with proper modification to hold probes) is shown, for example in U.S. Pat. No. 6,352,513, the disclosure of which is incorporated herein by reference.

In an exemplary embodiment of the invention, the system is used for pre-term births and monitoring thereof. For example, probes may be attached to a cervix of a mother before a due date. The mother may wear a system, as described above. Alternatively or additionally, the mother may periodically be attached (or go near) a system as described in FIG. 2. Such a system may be provided, for example, in a caregiver's office, at home or in a hospital or other clinic. Optionally, the mother wears a storage device that stores information, for later upload, for example, using methods well known in the art.

While the above has focused on normal birth, it should be appreciated these methods and apparatus may be used for other types of birth as well. For example, in the birth of twins, probes may be attached to the two twins in parallel or in series. Possibly, the cervical probes are left in place. Alternatively they may be reattached or replaced. In another example, probes may be attached to a leg and/or a buttocks of a fetus with a rear presentation. Alternatively or additionally, the probes may be used during an assisted birth (e.g., manual, vacuum, forceps), for example, to assess the effect of the assistance. The positioning of the probes may then vary over a normal vertex birth, so as to not interfere with the various assistance methods.

While the above description has focused on human birthing, it can also be applied to animal birthing, for example horses and cows.

The above application has focused on applications in the birth canal in which there are various specific problems of pressure, environment, movement, interference and communication. However, the presented systems and methods may be used for other intra-body applications, for example those in which other position sensors are used, for example one or more of:

(a) Tracking, for example of catheter, endoscope, biopsy needles, stereo tactic probes, ophthalmic probes, prostate probes, amniocentesis needles and/or invasive tools, for example in human or other animal blood vessels or lumens, for example with transponders at the tip or along the catheter. These may be used to guide procedures (e.g., trans-myocardial revascularization, eye surgery) or make measurements, for example of cardiac contractility (b) Tracking and detecting of wireless devices, for example a pill swallowed for imaging a GI tract and implanted drug delivery devices of various kinds. This tracking may be used, for example, to assess progress and/or to generate alerts if the device wanders into a danger zone.

Alternatively or additionally, external medical application can be provided, for example, assessment of joint motion, for example using implanted or external probes.

As can be appreciated, depending on the type of configuration and mode, the information provided about a transponder can be 1, 2, 3, 4, 5, or 6 dimensional information, selected from positional and/or orientation information.

It will be appreciated that the above described methods and devices of transponder excitation and reception and birth monitoring may be varied in many ways, including, changing the order of steps and the exact materials and circuits used for the devices. In addition, a multiplicity of various features, both of methods and of devices have been described. It should be appreciated that different features may be combined in different ways. In particular, not all the features shown above in a particular embodiment are necessary in every similar exemplary embodiment of the invention. Further, combinations of the above features, from different described embodiments are also considered to be within the scope of some exemplary embodiments of the invention. In addition, some of the features of the invention described herein may be adapted for use with prior art devices, in accordance with other exemplary embodiments of the invention. The particular geometric forms used to illustrate the invention should not be considered as necessarily limiting the invention in its broadest aspect to only those forms, for example, where a spherical probe is shown, in other embodiments an oval probe may be used. The methods and/or controller may be implemented in various ways, for example using dedicated hardware, software or firmware. The scope of the invention includes devices programmed and designs to carry out the methods and methods performed using the devices.

Also within the scope of the invention are kits which include sets of transducers, optionally color-coded and optionally a transmitter, a receivers and/or one or more disposable coverings. Measurements are provided to serve only as exemplary measurements for particular cases, the exact measurements applied will vary depending on the application. When used in the following claims, the terms "comprises", "comprising", "includes", "including" or the like means "including but not limited to".

It will be appreciated by a person skilled in the art that the present invention is not limited by what has thus far been described. Rather, the scope of the present invention is limited only by the following claims.

The invention claimed is:

1. A birth monitoring system, comprising:
    an ultrasonic transmitter comprising at least one transmission element;
    an electromagnetic RF receiver comprising at least one RF antenna;
    at least two transponders adapted to attach to a cervix and which generate RF signals responsive to excitation by an ultrasonic signal;
    a signal distinguisher which distinguishes between RF signals from different transponders; and
    a controller configured to analyzes said RF signals to produce an indication of a progress of a birth.

2. A system according to claim 1, wherein said indication comprises a dilation of said cervix.

3. A system according to claim 1, wherein said indication comprises a station of a fetal head.

4. A system according to claim 1, wherein said indication comprises an orientation of a fetal head.

5. A system according to claim 1, wherein said system is adapted to be worn by a mother being monitored.

6. A system according to claim 1, wherein said distinguisher is part of said controller.

7. A system according to claim 1, wherein at least one of the transponders comprises:
    an ultrasonic sensor that detects impinging ultrasonic waves and generates electrical signals in response thereto;
    an electrical connection which receives said signals; and
    an electromagnetic RF transmitter coupled to said electrical connection and which generates an RF signal in response to said detected waves.

8. A system according to claim 7, wherein said electrical connection comprises circuitry.

9. A system according to claim 8, wherein said circuitry comprises a driving circuitry.

10. A system according to claim 8, wherein said circuitry comprises a tuning circuitry.

11. A system according to claim 8, wherein said circuitry comprises a non-linear element which generates harmonics.

12. A system according to claim 8, wherein said circuitry modifies a frequency of said detected ultrasonic waves to generate a frequency for said transmitted RF waves.

13. A system according to claim 12, wherein said modifying comprises multiplying.

14. A system according to claim 12, wherein said modifying comprises a frequency shifting.

15. A system according to claim 12, wherein said circuitry comprises a variable element for generating different frequencies from a same base circuit.

16. A system according to claim 12, wherein said circuitry resonates with said impinging waves to generate said transmitted waves.

17. A system according to claim 12, wherein said circuitry comprises a modulation circuitry that uses said impinging waves to modulate said transmitted waves.

18. A system according to claim 12, comprising at least one additional sensor and wherein said circuitry modulates said transmitted wave using a signal from said sensor.

19. A system according to claim 7, wherein said electromagnetic RF transmitter has an output lower than said signal.

20. A system according to claim 7, wherein said electrical connection drives said RF transmitter with substantially no delay relative to said ultrasonic detection.

21. A system according to claim 7, wherein said at least one of the transponders comprises a covering adapted to protect said transponder from fluids and pressures extant in a birth canal.

22. A system according to claim 21, wherein said covering is disposable.

23. A system according to claim 7, wherein said transponder is powered solely by said detected ultrasonic waves.

24. A system according to claim 7, wherein said at least one of the transponders is powered by a transmitted power field.

25. A system according to claim 7, wherein said at least one of the transponders is powered by an integral power source.

26. A system according to claim 7, wherein said at least one of the transponders comprises a separate transmission antenna spatially displaced from said sensor by a wire, to a distance at least 10 times a maximal dimension of said sensor.

27. A system according to claim 26, wherein said wire is long enough to reach from a cervix to outside of a body, through a birth canal.

28. A system according to claim 27, wherein said birth canal is a human birth canal.

29. A system according to claim 27, wherein said birth canal is an equine or bovine birth canal.

30. A system according to claim 1, wherein at least one of the transponders is small enough to avoid interfering with a birth process, when implanted in a birth canal.

31. A system according to claim 1, wherein at least one of the transponders comprises an integral anchor adapted for attachment to cervical tissue.

32. A system according to claim 1, wherein at least one of the transponders comprises:
    a detection sensor;
    an anchor for attaching said sensor to a location of a body;
    at least one wire electrically coupled to said sensor; and
    a transmitter, electrically coupled to said at least one wire and adapted to be placed at a distance front said sensor, which distance is at least 10 times greater than a maximum dimension of said sensor.

33. A system according to claim 32, wherein said detection sensor is an ultrasound sensor.

34. A system according to claim 32, wherein the transmitter electrically coupled to said sensor comprises an electromagnetic RF transmitter.

35. A system according to claim 1, comprising a processor configured for determining a time of flight of said ultrasonic wave from a difference between a time of arrival of said RF wave and a time of transmission of said ultrasonic wave.

36. A system according to claim 1, wherein said distinguisher is capable of distinguishing between RF signals by their frequencies.

37. A system according to claim 1, comprising an ultrasonic transmitter capable of producing a broad band pulse, and each of the transponders respond to a different portion of said broad band pulse.

38. A system according to claim 1, wherein at least one of said transponders is configured to transmit RF waves having a frequency that is a small integer multiple of a frequency of said ultrasonic wave.

39. A system according to claim 1, wherein said RF receiver is near-field receiver.

40. A system according to claim 1, comprising a plurality of RF receiving antennas and a processor configured to determining phase information from RF signals received by the antennas.

41. A system according to claim 40, wherein said processor is configured to reconstructing an orientation of said transponder from said phase information.

42. A system according to claim 1, wherein at least one of said transponders is adapted for insertion in a body.

43. A system according to claim 42, wherein said transponder is adapted for insertion into tissue adjacent a birth canal.

44. A system according to claim 43, wherein said birth canal is a human birth canal.

45. A system according to claim 43, wherein said birth canal is an equine or bovine birth canal.

46. A system according to claim 1, wherein at least one of the transponders is adapted to be attached to a fetal head.

* * * * *